US012565668B2

(12) United States Patent
Pessoa et al.

(10) Patent No.: US 12,565,668 B2
(45) Date of Patent: Mar. 3, 2026

(54) USE OF BIOMAGNETISM FOR BIOGAS PRODUCTION

(71) Applicants: TECHNISCHE UNIVERSITÄT BERLIN, Berlin (DE); Federal University of Pernambuco, Recife (BR)

(72) Inventors: Matheus Pessoa, Berlin (DE); Matthias Kraume, Hohen Neuendorf (DE); Motta Sobrinho, Recife (BR)

(73) Assignees: Technische Universitat Berlin, Berlin (DE); Federal University of Pernambuco, Recife (BR)

( * ) Notice: Subject to any disclaimer, the term of this patent is extended or adjusted under 35 U.S.C. 154(b) by 846 days.

(21) Appl. No.: 17/787,343

(22) PCT Filed: Dec. 21, 2020

(86) PCT No.: PCT/EP2020/087411
§ 371 (c)(1),
(2) Date: Jun. 20, 2022

(87) PCT Pub. No.: WO2021/123417
PCT Pub. Date: Jun. 24, 2021

(65) Prior Publication Data
US 2023/0023082 A1 Jan. 26, 2023

(30) Foreign Application Priority Data

Dec. 20, 2019 (DE) .......................... 102019009105.1
Aug. 11, 2020 (DE) .......................... 102020121134.1

(51) Int. Cl.
*C12P 5/02* (2006.01)
*C12N 9/24* (2006.01)
*C12N 13/00* (2006.01)

(52) U.S. Cl.
CPC ............ *C12P 5/023* (2013.01); *C12N 9/2402* (2013.01); *C12N 13/00* (2013.01); *C12Y 302/01015* (2013.01)

(58) Field of Classification Search
CPC ....... C12P 5/023; C12N 9/2402; C12N 13/00; C12Y 302/01015; C12M 35/06; C12M 35/08; C12M 45/02; C12M 45/09; Y02E 50/30
See application file for complete search history.

(56) References Cited

FOREIGN PATENT DOCUMENTS

DE 102012022178 A1 5/2014
WO WO-2018134391 A1 * 7/2018

OTHER PUBLICATIONS

Aldin S et al. Modeling the Effect of Sonication on the Anaerobic Digestion of Biosolids. 2010. Energy Fuels. 24, 4703-4711. (Year: 2010).*
Alkaya E et al. Anaerobic mesophilic co-digestion of sugar beet processing wastewater and beet pulp in batch reactors. 2011. Renewable Energy. 36, 971-975. (Year: 2011).*
Schimpf U et al. Improving the Efficiency of Large-Scale Biogas Processes: Pectinolytic Enzymes Accelerte the Lignocellulosic Degradation. 2013. Journal of Sustainable Energy & Environment. 53-60. (Year: 2013).*
Int'l Search Report for PCT/EP2020/087411, dated Apr. 26, 2021.
A. Haritwal, et al., "Study on the Improved Biagas Generation Through Magnetic Field Modified Anaerobic Digestion", Int'l Journal of Engineering Research & Technology, vol. 4, No. 5, May 26, 2015 (May 26, 2015), pp. 1175-1179.
M. Zablodskiy, et al., "The Influence of a Rotating Magnetic Field on the Intensity of Methane Formation in a Bioreactor", 2019 IEEE 39th Int'l Conference on Electronics and Nanotechnology (ELNANO), IEEE, Apr. 16, 2019 (Apr. 16, 2019), pp. 507-511.
Y. Litti, et al., "Increasing the efficiency of organic waste conversion into biogas by mechanical pretreatment in an electromagnetic mill", Journal of Physics: Conference Series, vol. 1111, Dec. 2018 (Dec. 2018), p. 012013.
M. Zablodskiy, et al., "Intensification of Biogas Fermentation Processes in the Bioenergy System", 2018 IEEE 3rd Int'l Conf. on Intelligent Energy and Power Systems (IEPS). IEEE, Sep. 10, 2018 (Sep. 10, 2018), pp. 39-44.

* cited by examiner

*Primary Examiner* — Paul J Holland
(74) *Attorney, Agent, or Firm* — MaxGoLaw PLLC

(57) ABSTRACT

A method for improving a biogas production is provided in which an organic substrate is pretreated by various methods. In particular, the method includes a combination of a magnetic and an enzymatic pretreatment of the substrate with an attractive specific energy gain. The application of a magnetic field induces changes in biological systems.

17 Claims, 2 Drawing Sheets

Energy value of biomass [kWh/kgTS]
Energy Consumption of pretreatment [kWh/kgTS]
Energy net [kWh/kgTS]

USE OF BIOMAGNETISM FOR BIOGAS PRODUCTION

FIELD OF THE INVENTION

The invention relates to a method to produce biogas from organic substrates. The method has a number of steps that relate in particular to a pretreatment of the substrate. First, the organic substrate is provided. Then, the organic substrate is mixed with an enzyme to obtain an enzyme-substrate complex. In a next step, the enzyme-substrate complex is influenced by a magnetic field and then exposed by a defined temperature for a defined time. Finally, anaerobic digestion is initiated.

BACKGROUND OF THE INVENTION

Biogas is a climate-neutral alternative to natural gas. It is preferably obtained naturally through the decomposition of organic waste or renewable resources and therefore does not count as a fossil fuel. As a renewable source of energy, biogas is mainly compost of three gases: methane ($CH_4$), which its chemical energy is converted to mechanical energy, carbon dioxide ($CO_2$) and in a small proportion but with corrosion potential, hydrogen sulfide ($H_2S$).

The combustion of biogas can advantageously be $CO_2$-neutral because plants that are preferably fermented in a biogas plant have absorbed the same amount of $CO_2$ that is released during the subsequent combustion of biogas. This means that biogas does not cause any additional $CO_2$ emissions. Moreover, biogas is a good complement to the renewable energy sources wind and sun. Unlike wind and solar energy, biogas can be produced and stored regardless of the weather. This makes biogas an excellent choice providing baseload supply and balancing fluctuations in the power grid.

For these reasons, there is a high demand for the use and the production of biogas and a great need for continuous improvement.

In anaerobic digestion, the production of biogas is directly connected with the level of substrate degradability and its conversion to biogas. In order to reach a higher production, pretreatments are applied to the substrate (Organic waste, agricultural waste, manure, sludge) aiming at a higher conversion of its carbohydrates, fat and protein content into substrates for the bacteria consortium involved in every step (hydrolysis, acidogenesis, acetogenesis and methanogenesis) for the formation of biogas.

The whole of pretreatments in anaerobic digestion is related to the change in complex substrate structures that weakens carbohydrate-lignin bonds, decreasing its degree of polymerization, increasing particle surface area, particle size reduction, solubility of substrate content, biodegradability enhancement, formation of refractory compounds and loss of organic material. Pretreatments in anaerobic digestion can be classified as thermal, ultrasonic, freeze/thaw, chemical, other mechanical, microwave, wet oxidation, pulsed electric field treatments and biological.

However, all the pretreatments described and known from the state of the art did not lead to a sufficient increase in enzymatic activity and thus to a significant improvement in biogas production. In addition, many of the pretreatments require disadvantageously increased amounts of energy:

Problem Addressed by the Invention

The problem addressed by the invention is thus to avoid the disadvantages of the prior art and to provide a method for improving the production of biogas, in particular increasing the biogas quantity and quality, whereby only a small amount of energy is required for this purpose.

SUMMARY OF THE INVENTION

The problem addressed by the invention is solved by the features of the independent claims. Advantageous embodiments of the invention are described in the dependent claims.

The invention relates to a method to produce biogas from organic substrates comprising:
- a. Providing an organic substrate;
- b. Mixing the organic substrate with an enzyme to form an enzyme-substrate complex;
- c. Exposing the enzyme-substrate complex to an induced magnetic field as a magnetic pretreatment;
- d. Exposing said magnetically treated enzyme-substrate complex to a first temperature $T_1$ for a first time $t_1$;
- e. Initiating an anaerobe digestion.

The method described is to be seen as a significant turning away from the prior art. In particular, the method comprises a number of pretreatment processes for the organic substrate which were not yet known in this combination and sequence. The combination of the present method steps leads to a surprising synergistic effect, which results in the advantageous properties and the associated overall success of the invention, whereby the individual features interact with each other. An important advantage of the process according to the invention is the extremely increase of the enzymatic activity and reach higher substrate degradation for biogas production. This increases the amount of biogas and the quality, wherein the quality is especially defined by a high methane volume.

The purpose of the invention is preferably to expose an enzyme-substrate complex to an induced magnetic field in the weak range aiming at an increase in enzymatic activity, substrate degradability and consequently, more methane production. A magnetic field facility (MFF) demands a low energy input; therefore, a positive energy balance can be achieved. The main idea preferably consists of applying the process of increasing enzymatic activity through magnetic field exposure aiming at a higher biogas production with a higher specific energy gain. The magnetic field application is preferably restricted to the pretreatment of the substrate, not during fermentation.

As anaerobic digestion is composed of four steps (Hydrolysis, acidogenesis, acetogenesis and methanogenesis), wherein the invention preferably focusses in the first and last step (hydrolysis and methanogenesis). The first step (Hydrolysis) is related to how the substrate (organic waste) is decomposed, from long chain structures to small chain sugars that will feed the bacteria consortium involve in this process. The last step (Methanogenesis) is related to the use of the intermediate products (from the previous steps) to form biomethane.

Preferably, the term "organic substrate" refers to the raw material used in a biogas plant to produce biogas. Occasionally, the term "fermentation substrate" is also used in the prior art. Biomass with a high water content that cannot be directly thermally utilized is particularly suitable as a substrate. Biomass rich in cellulose (e.g., straw) and lignocellulose (wood) are poorly accessible for microbial degradation and therefore not suitable as a substrate for biogas production without prior degradation of the cellulose by bioextrusion. In bioextrusion, a substrate is preferably squeezed, pressed and crushed by the action of mechanical energy under high pressure and temperature. The mass to be processed is then abruptly relaxed, resulting in the rupture of the cell structure, a lignin phase.

In biogas plants, anaerobic microbial degradation (fermentation) of the organic substrate takes place. The organic substrate serves as a source of nutrients and energy for the microorganisms. The gaseous methane separates from the substrate and can be used, for example, in a combined heat and power plant to generate electricity and heat. The main components of biogas, methane ($CH_4$) and carbon dioxide ($CO_2$), are on the one hand metabolic waste of the microorganisms, on the other hand the energy-rich methane is the main product of a biogas plant. The residual material (liquid and/or solid) remaining after fermentation is called digestate and can be advantageously used as a nutrient-rich organic fertilizer.

In a further preferred embodiment, another material (additive) is used in addition to a main substrate, which is co-fermented as a co-substrate. Especially in biogas plants that are mainly operated with liquid manure, co-substrates such as residues from grease traps can advantageously provide a large share of the methane yield.

In biogas plants, renewable raw materials as well as residues from animal husbandry and biogenic waste are used as substrate. In general, almost all substances of organic origin are suitable for fermentation in biogas plants. The less water and inorganic matter and the more easily degradable substances such as fats, proteins and carbohydrates are in the substrate, the more methane can potentially be produced from it. As already indicated, fibrous substrates with difficult to degrade carbon compounds such as lignocelluloses (wood) are unsuitable because they are almost exclusively and very slowly degraded by aerobic fungi. To estimate the gas formation potential, the methane yield is related to the organic fraction of the dried input mass.

The magnetic pretreatment is preferably responsible to alter properties of the exposed enzyme-substrate complex like polarization, ordering of particles, molecule structure, changes in electric charge. The application of an induced magnetic field on the enzyme-substrate complex can be established by placing the magnetic field facility (MFF) near the enzyme-substrate complex, preferably in combination with mechanical pretreatment (e.g., cutting down the substrate into smaller pieces) or also by continuously pumping the enzyme-substrate complex (in the form of a solution) through a magnetic field facility.

In a further preferred step, said magnetically treated enzyme-substrate complex is exposed to a first temperature $T_1$ for a first time $t_1$. This advantageously leads to the initiation of an enzymatic pretreatment. Enzymatic pretreatment is advantageously performed with low energy input and without producing chemical residues.

Enzymes are generally proteins that act as biological catalysts in certain material reactions and degradation processes as well as in synthesis. Usually, these enzymes are produced by the microorganisms involved themselves. Therefore, the required enzyme concentrations in an optimally functioning fermenter are sufficiently ensured by the enzyme production of the microorganisms. By adding certain enzymes by a pretreatment, plant components that are difficult to degrade can be broken down more quickly, thus improving the productivity of the overall process. In addition, enzymes in pretreatment lead to many other benefits, namely: Faster and more intensive digestion of the biomass; Reduction of viscosity and thus reduced stirring energy costs; Increase in productivity or biogas rate; Savings in substrate costs; Accelerated degradation of cellulose and hemicellulose; Dissolution of floating layers in the fermenter; Dissolution and liquefaction of large accumulations of solid matter (hay, grass silage, solid manure); Avoidance of massive floating layers in a final storage.

In a further preferred embodiment, the method is characterized in that in a step following said step d, the enzyme-substrate complex is exposed under a preferred high temperature of preferably 60° C.-120° C., more preferably 80° C.-120° C., in particular 100° C. These temperature ranges cause the enzymatic reaction to stop. The optimum action for most enzymes is between 30 and 45° C.; at temperatures below 10° C. or above 60° C., most enzymes no longer work. Furthermore, the temperatures advantageously lead to drying of the substrate, with the enzyme-substrate complex preferably being under the influence for 48 h at the preferred said temperatures.

In another preferred embodiment the method is characterized in that said step d. is followed by (i) Providing an additive;

(ii) Mixing said enzyme-substrate complex with said additive to form a fermentation broth;

(iii) Introducing said fermentation broth into a bioreactor to produce biogas, resulting in initiating an anaerobe digestion.

The use of additives leads to a number of advantages, especially in the fermentation process. Various parameters of the fermentation process can be changed by the additives so that a better biogas production is achieved. The choice of additive is preferably dependent on the substrate used. This will become clear in the following.

As explained at the beginning, the fermentation and especially the methane gas production in biogas production involves methanogenic archaea (methane producers). In this system of interlocking physical, chemical, biochemical and microbiological steps, a large number of different specialized microorganisms work together, some of them with very different requirements for the degradation of organic substances, ultimately to methane gas and carbon dioxide The microorganisms involved in these processes, like all living organisms, first need nutrients, the so-called trace elements, to maintain the metabolism and for their own reproduction. These elements are: Hydrogen (H), Carbon (C), Nitrogen (N), Oxygen (O), Phosphorus (P) and Sulfur (S). In addition, a sufficient availability of e.g. sodium (Na), potassium (K), calcium (Ca), iron (Fe) and magnesium (Mg) is of great importance for the microorganisms. Biogas plants basically need micronutrients and trace elements, which usually come from the substrate, but are often not available in sufficient quantities. The preferred use of micronutrients as additives may not produce more energy from the fermentation broth, but fermentation can advantageously be accelerated, and the biogas process is advantageously more stable and predictable. In addition, larger loadings in the bioreactor and thus higher biogas yields can be achieved.

It should also be noted that biogas contains $H_2S$, which, as an acid gas, has an acute toxic effect not only on humans and animals but also on many microorganisms in the fermenter and can thus inhibit methane formation. Furthermore, an increased hydrogen sulfide content leads to corrosion of plant components. By adding iron(II) and iron(III) salts (e.g. $FeCl_2$, $FeSO_4$, $FeCl_3$, $Fe(OH)_3$) as an additive, sulfide can be specifically precipitated in the fermentation tank so that it does not enter the biogas as hydrogen sulfide.

In addition to hydrogen sulfide, ammonia can also be present as a toxic gas in low concentrations in the biogas. It is formed preferably during the breakdown of proteins and other nitrogenous compounds such as urea or uric acid in animal excrements. The ammonia concentration in the biogas process is strongly dependent on the pH value, the temperature and the ammonium concentration in the fermentation broth.

To remedy a high ammonium or ammonia concentration, mineral preferred substances are used as additives. These advantageously cause the ammonium ions to absorb and bind. Zeolites and aluminosilicates, also known as molecular sieves, are preferably used, or clay minerals are preferably used for the sorption of ammonia. These are natural products that have pores and can thus fix ammonia by ionic forces. In this process, cations such as potassium, calcium or magnesium are replaced from the lattice structure and exchanged for ammonium as in an ion exchanger. Ammonium thus remains bound to these solids and is thus removed from the system.

Methane formation in the biogas process requires preferably a stable pH value. The pH value is primarily influenced by the bases and carbonate concentration or the lime-carbonic acid equilibrium, which determines the carbonate buffer and thus the buffer capacity in the fermenter. In addition, the ammonium/ammonia system can contribute to the buffer capacity. If the carbonate buffer capacity is sufficiently large, the formation of organic acids during acidogenesis and acetogenesis has little effect on the pH. If high amounts of carboxylic acids continue to be formed in the process, the basic buffering capacity will eventually be exhausted, and acidification of the fermenter contents may occur very rapidly.

Buffering substances such as sodium hydrogen carbonate or combination preparations with trace elements and carbonates are preferably used as additives to stabilize the pH value in the event of possible acidification.

The additives are preferably chemicals that provide an alkaline environment.

Specially digested brown algae or alginates are intended to create an optimal nutrient medium for the bacteria during biogas production and thus increase the methane yield. Therefore, in a further preferred embodiment, brown algae or alginates can used as additives.

For purposes of the invention, bioreactor refers to any manufactured device or system that supports a biologically active environment. For instance, a bioreactor is a vessel in which a chemical process is carried out involving organisms or biochemically active substances derived from such organisms. This process can be either aerobic or anaerobic. These bioreactors are preferably cylindrical, range in size from liters to cubic meters, and are preferably made of stainless steel. A "bioreactor" is also referred to as a "fermenter" in this document.

Preferably, the sequence of above-mentioned steps (i)-(iii) can also be carried out after said temperature treatment to stop the enzyme reaction.

In a further preferred embodiment, the method is characterized in that the additive is a sewage sludge. The sewage sludge gives advantageous stability to the fermentation process. For an advantageous fermentation process, sewage sludge has a high buffer capacity when used as an additive. Sewage sludge consists of organic and mineral substances, which in turn are present in dissolved and solid form. These have in particular many good nutrients for the microbacteria included in the fermentation process.

In a further preferred embodiment, the method is characterized in that a sonication pretreatment is performed before method step b. The principal behind sonochemistry has its origins from acoustic cavitation, which involves formation, growth and implosive collapse of bubbles in a liquid. The cavities in sonication happens when the molecules of a liquid are distancing from each other as a result of an applied under-pressure (negative pressure) culminating in the formation of voids or cavities, then cavitation bubbles will be formed. Considering an ongoing input of energy, the bubbles will increase in size and at some point the cavity structure won't be stable resulting in collapse and the accumulated energy release. The frequency of the sound wave is inversely proportional to its bubble critical, meaning that bigger bubbles are generated from low frequency ultrasound (20 kHz) being about 100 to 170 μm, although small bubbles in the range of 3.3 μm are produced by big frequency ultrasound (1 MHz). The shear stress resulting from this collapse provoke cell lysis i.e. cell wall wrecking and consequently its content release into the solution.

Sonication is therefore advantageous exactly controllable to meet the optimal process parameters of the enzyme and/or the substrate.

The rate of biochemical reactions can be advantageously enhanced by sonication, depending on intensity and time duration, sonication in cell and protoplast for protein synthesis can be stimulated, inhibited or remain unaltered. At low ultrasound intensity the protein synthesis can be enhanced, although a decrease is observed at high intensities.

The lignin-cellulose hydrophobic interactions may be disrupted by sonication prior to enzymatic hydrolysis increasing its conversion to fermentable sugars. Sonicated assisted pretreatment of lignocellulosic material could increase the sugar yield compared with control samples without sonication. Ultrasound waves also may induce conformational changes in enzyme molecules, enabling its structure more apt to combine with substrate and exerting also a catalytic function, in the case of the invention, sonication is preferably applied prior to enzymatic hydrolysis.

In a further preferred embodiment the method is characterized in that the method step d comprises placing the enzyme-substrate complex in an incubator, wherein the time $t_1$ is in a range of 10 to 56 h, preferably in a range or 24-48 h and in particular the time $t_1$ is 48 h and/or the temperature $T_1$ is between 35° C.-60° C., preferably between 45° C.-55° C. and in particular the temperature $T_1$ is 50° C. Excellent enzyme activity is achieved at the preferred values described. The incubation time and temperature depend, among other things, on the enzyme and the substrate used in the enzyme-substrate complex.

The incubation time ($t_1$) is particularly preferred to be seen at 48 h, but can also be 24 h, since the increase in soluble sugars does not increase dramatically between 24 and 48 h.

The incubation temperature for the enzyme is 50° C., which is the optimum temperature for example for pectinase. The application of this process to other enzymes may be applied in other temperature.

In a further preferred embodiment, the enzyme-substrate complex is preferably mixed during the incubation period. It can be preferably done in different ways, like by a magnetic stirrer, normal mixer and etc.

It should be noted that steps b and c of the method according to the invention are preferably carried out at room temperature (20° C.+/−4° C.), otherwise the enzymes would be already active.

In another preferred embodiment, the enzyme-substrate complex is provided in an incubator under the above conditions at an operation of 20 Hz (rotation frequency).

In a further preferred embodiment, the method is characterized in that method step b comprises:

(i) Providing an enzyme solution, wherein an enzyme in the form of a powder is mixed with ultrapure water (ii) Mixing the enzyme solution with the organic substrate to form the enzyme-substrate complex.

wherein the organic substrate is ground and mixed with the enzyme solution by a magnetic stirrer for a time $t_2$ and/or the enzyme is pectinase from *Aspergillus niger.*

It is understood that other enzymes can also be used, especially depending on the substrate. For the inventors, however, pectinase from *Aspergillus niger* has shown particularly good properties in terms of improved enzyme activity under the influence of a magnetic field. In particular, in combination with a substrate such as sugar beet pulp, an improved biogas reaction could take place.

A magnetic stirrer is preferably an electrical device used in chemical laboratories for stirring liquids. It is preferably a laboratory device that employs a rotating magnetic field to cause a stir bar (or flea) immersed in a liquid to spin very quickly, thus stirring it. Preferably, the magnetic stirrer also includes a heating plate that can be used to heat the liquid. The use of a magnetic stirrer has the advantage that the temperature can be set relatively precisely and can be controlled, for example, by a temperature controller that is switched on. The heat supplied is advantageously distributed quickly and evenly in the container contents by the stirring motion. Advantageously, reproducible mixing qualities are achieved by preferably programmable mixing sequences. Furthermore, a magnetic stirrer is advantageously used due to its simplicity and cost.

Preferably, other mixing devices can also be used, such as a mixing motor.

In a further preferred embodiment, the method is characterized in that the time $t_2$ is in a range of 2-20 min, preferably in a range of 5-15 min and in particular the time $t_2$ is 10 min. Due to the preferred time ranges, an optimal mixing can be achieved. Advantageously, a very stable enzyme-substrate complex is thus formed, with little energy having to be input for stirring.

In a further preferred embodiment, the method is characterized in that the magnetic pretreatment comprises the following steps:

(i) Providing a magnetic field (ii) Influencing the enzyme-substrate complex by the magnetic field for a time $t_3$.

The activity of certain enzymes can be advantageously increased by a magnetic field. The principle behind the enlarged activity is preferably attributed to the radical pair mechanism i.e. the mechanism responsible for the changes in reaction kinetics induced by a magnetic field, or also due to conformational changes of the enzyme as a consequence of an increase in helicity of the polypeptide backbone of the hydrogen bonding.

The mechanism by which magnetic field interactions with biological systems takes place is related to radical pair recombination magnetic sensitivity. Considering a low viscosity solution, an encounter of radical pairs in singlet state almost always result in reaction, on the other side, events regarding radical pairs in triplet state will not produce bond formation.

In a further preferred embodiment the method is characterized in that the magnetic field has a magnetic flux density of a range smaller than 1 mT, and in particular a magnetic flux density of 0.2 mT and/or the time $t_3$ is in a range of 2-6 h, preferably in a range of 3-5 h and in particular the time $t_3$ is 4 h. A weak magnetic field has the advantage that it requires only a very small energy input. It has been shown that the weak magnetic field is already sufficient to generate an influence on the enzyme-substrate complex. Furthermore, it has been shown that coils are more durable if they only have to apply a weak magnetic field.

The application of an induced magnetic field can take place by several ways, like by electric currents, AC (time-varying magnetic field), DC current (static magnetic field) or permanent magnets.

Preferably, a solenoid coil with direct current (DC) is used. The fields smaller than 1 mT are preferably classified as weak fields, between 1 mT to 1 T are preferably moderate fields, strong (1 T to 5 T) and higher the 5 T are classified preferably as ultra strong fields. It should be noted that the type of current may preferably have an influence on the result of the enzymatic action. If an AC current is used, the result may not be the same (compared to DC current), as the AC current induces an electric field in addition to a magnetic field A moderate static magnetic field (non-time varying) can induce advantageously effect in biological systems due to due to deformed sodium (at some degree) and ions channels, affecting their activation energy as a result of a re-orientation of the diamagnetic membrane phospholipids In the case of a time-varying magnetic field where an electric field takes place, an electronconformational coupling may take place considering enzymatic systems, specifically in membrane structures, a high and medium periodic electric potential are received and processed. This leads to a conversion of electric field energy into chemical potential energy if the system properties regarding field frequency and strength are fulfilled. This may have a beneficial effect on enzymes such as lipoxygenase and polyphenol oxidase, where significant effect has been observed.

In a further preferred embodiment, the method is characterized in that the sonication pretreatment comprises the following steps:

(i) Affecting the organic substrate by ultrasound;

(ii) Cooling the organic substrate with iced water during the sonication pretreatment.

Ultrasound does affect the substrate, letting it more degradable for biogas production, but with a higher energy demand as the magnetic field, therefore the inventors used the ultrasound in combination with the above-mentioned pretreatment and not as a main pretreatment.

Pretreatment by sonication additionally leads to a number of advantages, namely: it allows increased mass transfer; it is linearly scalable; the process is safe and easy to operate; the process is low maintenance and environmentally friendly.

The cooling of the organic substrate is preferably performed because during sonication temperature and pressure can increase and may change the outcome. This step is especially used when an ultrasonic finger is used as the sonication device. However, if an ultrasonic bath is used, this step may not be necessary.

In a further preferred embodiment, the method is characterized in that the organic substrate is sugar beet pulp.

The organic substrate used according to the invention is preferably sugar beet pulp, which is an agricultural waste from sugar production. However, the process can also be applied to other organic substrates such as corn, corn straw, rapeseed, grain, waste from soy production, rice straw, waste from sugar cane production, etc. In principle, the process can be applied to any organic matter. But for application to other substrates, the same or different enzymes are used and for each different enzyme, the configuration of magnetic field parameters (intensity and duration) may change.

Basically, when using the method according to the invention, the enzyme to be used in the process is preferably determined by examining the substrate-polysaccharide composition. In the case of sugar beet pulp (SBP), pectinase was chosen because of the large amounts of pectin in its composition.

Sugar beet pulp (SBP) can preferably be obtained as dry pellets with 95% total solids (TS) content. They are preferably stored at room temperature (20±4° C.) and ground into 2 mm pieces before use.

In a further preferred embodiment, the method is characterized in that the fermentation broth is operated for a time $t_4$ at a mesophilic temperature $T_2$ in the bioreactor and/or Calcium carbonate is dissolved as an additive in the fermentation broth. Calcium carbonate is preferably used as an alkaline correction chemical to keep the fermentation broth advantageously with a pH around 7 to 8.

In a further preferred embodiment the method is characterized in that the time $t_4$ is in a range of 15-30 days, preferably in a range or 19-23 days and in particular the time $t_4$ is 21 days and/or the temperature $T_2$ is between 20° C.-45° C., preferably between 30° C.-39° C. and in particular the temperature $T_2$ is 37.1° C. The mesophilic range is intended to provide more stable biological process conditions. This is advantageous stable range for the bacteria that participate in the process of fermentation.

In a further preferred embodiment, the bioreactor operates in a continuous mode. It is understood that in this mode a fermentation broth and/or substrate is continuously fed and fermentation residues are removed. The time ranges $t_4$ described above can therefore also be different.

In a further preferred the temperature $T_2$ can also be in a thermophilic range (preferably 41 to 122° C.). The thermophilic range, on the other hand, advantageously leads to a particularly fast process of biogas production, which also generates a larger gas volume.

For temperatures $T_2$ in both the mesophilic and thermophilic ranges, the temperature should preferably be kept as constant as possible during time $t_4$.

In a further preferred embodiment the method is characterized in that the bioreactor is a stainless-steel bioreactor and/or comprises a mixing system which is composed of two 45° pitched blade turbine and/or Sodium bicarbonate is added to the bioreactor prior to the production of biogas and/or Nitrogen is purged in the bioreactor for a time $t_5$ prior to the production of biogas, wherein the time $t_5$ is in a range of 20-40 min, preferably in a range or 25-35 min and in particular the time $t_5$ is 30 min. The blades pitched in the mentioned range lead to an advantageous flow around the outer drive broth, whereby this results in a constant mixing The nitrogen is preferably used to make an $O_2$ free atmosphere, otherwise anaerobic digestion would not occur. This step is used on the commissioning of biogas experiments as creating the proper conditions for the microorganisms involved in anaerobic digestion.

In a further preferred embodiment, the method is characterized in that the blade turbine comprises 6 blades and is preferably operated during the production every hour for 10 min at 90 rpm and once a day at 114 rpm. It is understood that the bioreactor may also have other parameters. For example, it can preferably have 2-8 blades or even more preferably 3, 5 or 7. The number of revolutions can also be adjusted accordingly.

The mixing system was designed for the configurations of the bioreactor used in the experiments, to ensure that the fermentation broth is well mixed. This configuration is not inherent for the success of the pretreatment because it depends on the geometry of the bioreactor/fermenter and will change according the volume of the reactor.

In a further preferred embodiment, the method is characterized in that the sewage sludge is in anaerobic condition at temperature $t_6$, wherein the temperature $t_6$ is room temperature and is in a range of 16° C.-24° C., in particular at 20° C. Anaerobic sewage sludge is preferably collected from wastewater treatment plant. The Sludge after anaerobic digestion is preferably chosen due to its negligible biogas potential and buffer capacity. After collection, the material is preferably kept nearly in anaerobic conditions at room temperature (20±4° C.).

In the following, the invention is explained in more detail with reference to figures, without being limited to them.

DETAILED DESCRIPTION OF THE FIGURES

Figure 1:
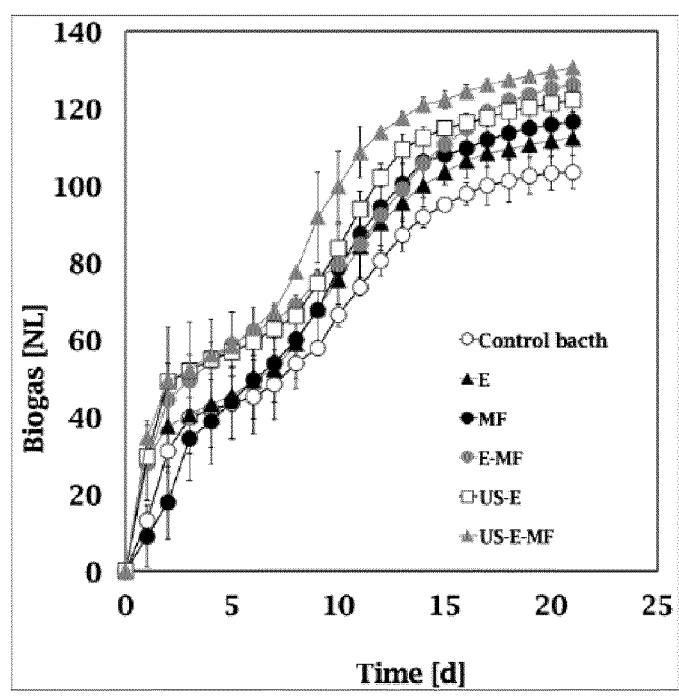
FIG. 1 Diagram of accumulated biogas production in standard liters (comparison of different pretreatment methods)

FIG. 1 illustrates a diagram of accumulated biogas production in standard liters, comparing substrates with different pretreatment methods. (Error bars calculated from the duplicate of various pretreatments and the control batch [21 days; 37.1° C.])

The different comparison variants are designated as follows in FIG. 1:

| Pretreatment | Nomenclature |
| --- | --- |
| Enzyme | E |
| Magnetic field | MF |
| Enzyme + Magnetic field | E-MF |
| Ultrasound + Enzyme | US-E |
| Ultrasound + Enzyme + Magnetic field | US-E-MF |

Biogas production presented a clear tendency in the batch tests (FIG. 1). The biogas production increases as more pretreatments are applied. The biogas volume increased by 26±4.4%, for the combination of three pretreatments (US-E-MF) in comparison to the control batch. Data analysis shows that a statistical test was performed and indicates that the pretreatments E-MF, US-E and US-E-MF presented statistical differences in comparison with the control, which was not the case for E and MF when applied alone. Analyzing all experiments involving enzymes, i.e., comparing the enzymatic pretreatment to its combination with MF, US and both together, E-MF and US-E-MF presented statistical difference, but for US-E the null hypothesis could not be rejected, i.e., there is no significant difference between the mean value of the enzymatic pretreatment batch (E) and the mean value of US-E.

Figure 2:
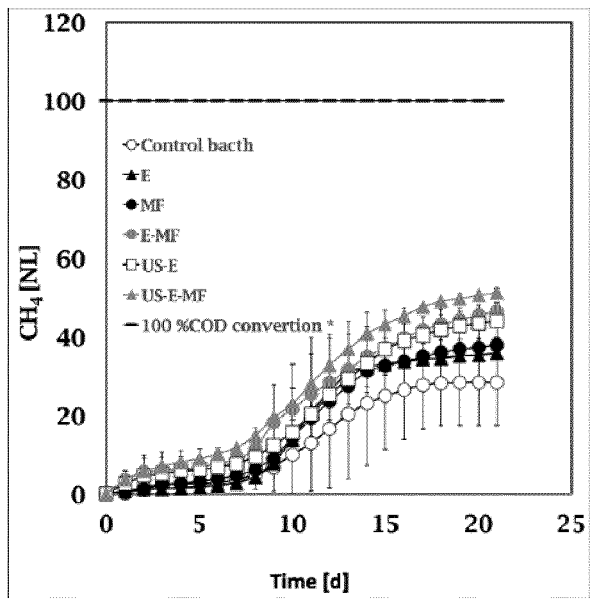
FIG. 2 Diagram of accumulated methane production in standard liters (comparison of different pretreatment methods)

FIG. 2 illustrates a diagram of accumulated methane production in standard liters, comparing substrates with different pretreatment methods. (Error bars calculated from the duplicate of various pretreatments and the control batch [21 days; 37.1° C.])

The conversion of 100% of the substrate COD (chemical oxygen demand) to methane, was calculated based on the assumption that, in standard conditions (0° C.; 1 atm) 1 g of COD yields 354 mL of methane.

TABLE 3

| Maximum theoretical methane potential. | | | |
|---|---|---|---|
| | $COD_{measured}$ | $COD_{batch}$ [gCOD] | Maximum theoretical potential [$L_{CH4}$] |
| SBP (220 g) | 1.121 [gCOD/gVS$_{SBP}$] | 284.02 | 100.54 |
| SS (11 L) | 40 [mg/mL] | 4.4 | 1.5 |
| | $\Sigma$ | 288.42 | 102.1 |

The different comparison variants are designated as follows in FIG. 2:

| Pretreatment | Nomenclature |
|---|---|
| Enzyme | E |
| Magnetic field | MF |
| Enzyme + Magnetic field | E-MF |
| Ultrasound + Enzyme | US-E |
| Ultrasound + Enzyme + Magnetic field | US-E-MF |

The methane production also increased in comparison to the control batch. Methane production from the combination of three pretreatments (US-E-MF) was 79±3.2% (244.6 NL/kgVS) greater than the control batch measurement, followed by E-MF (62±5.08%) (221.7 NL/kgVS) (FIG. 2). The control batch yielded 136 NL/kgVS; the enzymatic pretreatment (E) yielded 171.1 NL/kgVS; MF (180.7 NL/kgVS); and US-E (210.1 NL/kgVS). Data analysis for methane production followed a similar tendency compared to the biogas production. The pretreatments E-MF, US-E and US-E-MF presented significant difference in comparison with the control batch while MF and E did not. The pretreatments with enzymes, i.e., comparing the enzymatic pretreatment to its combination with MF, US and both together, did not present significant differences, i.e., there is no significant difference between the enzymatic pretreatment and its variation with MF, US and both together.

Figure 3:
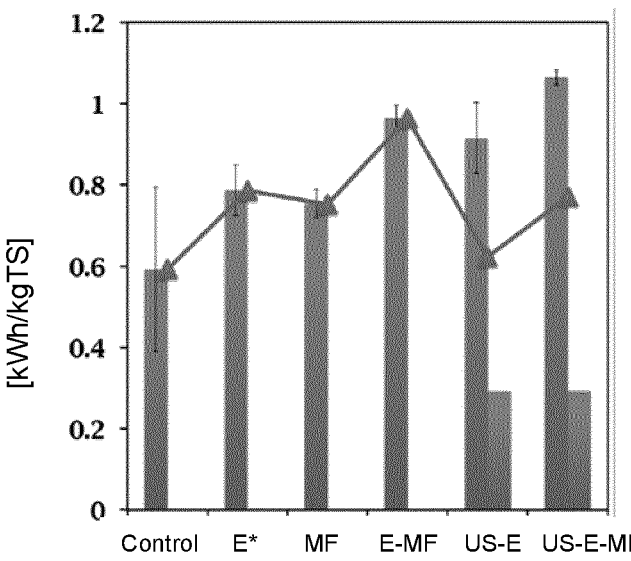
FIG. 3 Diagram of specific energy gain for batch experiments

FIG. 3 illustrate a diagram of specific energy gain for batch experiments

The energy balance of the batch experiments compares the energy from the methane content produced by the pretreatment subtracted from the energy consumed to perform the same pretreatment. The energy net (FIG. 3) indicates that the magnetization of the enzyme-substrate mixture (E-MF) exhibit the greatest balance. The energy consumed to perform the E-MF pretreatment accounted for 0.15% of the energy produced for the same pretreatment, while its variation with sonication (US-E-MF) accounted for 27.53%. Hence, the method according to the invention is able to use a negligible energy input and achieve the high level of biogas/biomethane. The magnetic field pretreatment (MF) accounted for 0.19% of its energy production and the sonication pretreatment followed by enzymatic pretreatment (US-E) accounted for 31.89% of its energy production. In the present case, the application of sonication before E-MF increased biogas and methane production. However, sonication demands a higher energy input than the magnetic field facility resulting in a lower specific energy gain.

The invention claimed is:

1. A method to produce biogas from organic substrates comprising:
   providing an organic substrate;
   mixing the organic substrate with an enzyme to form an enzyme-substrate complex;
   exposing the enzyme-substrate complex to an induced magnetic field as magnetic pretreatment, wherein the magnetic pretreatment comprises
   (i) providing the magnetic field; and
   (ii) influencing the enzyme-substrate complex by the magnetic field for a time $t_3$, wherein the induced magnetic field is provided by solenoid coil with direct current, wherein the enzyme-substrate complex is influenced by the magnetic field for a time $t_3$, wherein $t_3$ is in a range of 2-6 h and the magnetic field has a magnetic flux density of a range smaller than 1 mT;
   exposing said magnetically treated enzyme-substrate complex to a first temperature $T_1$ for a first time $t_1$ in an incubator, wherein the time $t_1$ is in a range of 10 to 56 h and temperature $T_1$ is between 35° C.-60° C.; and
   initiating an anaerobe digestion.

2. The method according to claim 1 characterized in that the exposing said magnetically treated enzyme-substrate complex to a first temperature $T_1$ for a first time $t_1$ is followed by
   (i) providing an additive;
   (ii) mixing said enzyme-substrate complex with said additive to form a fermentation broth; and
   (iii) introducing said fermentation broth into a bioreactor to produce biogas, resulting in initiating an anaerobe digestion.

3. The method according to claim 2 characterized in that the additive is a sewage sludge.

4. The method according to claim 1 characterized in that a sonication pretreatment is performed before the mixing step.

5. The method according to claim 1 characterized in that said mixing step comprises:
(i) providing an enzyme solution, wherein an enzyme in the form of a powder is mixed with ultrapure water;
(ii) mixing the enzyme solution with the organic substrate to form the enzyme-substrate complex; P1 wherein the organic substrate is ground and mixed with the enzyme solution by a magnetic stirrer for a time $t_2$ and/or the enzyme is pectinase from *Aspergillus niger*.

6. The method according to claim 5 characterized in that the time $t_2$ is in a range of 2-20 min.

7. The method according to claim 4 characterized in that the sonication pretreatment comprises:
(i) affecting the organic substrate by ultrasound; and
(ii) cooling the organic substrate with iced water during the sonication pretreatment.

8. The method according to claim 1 characterized in that the organic substrate is sugar beet pulp.

9. The method according to claim 2 characterized in that the fermentation broth is operated for a time $t_4$ at a mesophilic temperature $T_2$ in the bioreactor and/or Calcium carbonate is dissolved as an additive in the fermentation broth.

10. The method according to claim 9
characterized in that
the time $t_4$ is in a range of 15-30 days and/or the temperature $T_2$ is between 20° C.-45° C.

11. The method according to claim 2
characterized in that
the bioreactor is a stainless-steel bioreactor and/or comprises a mixing system which is composed of two 45° pitched blade turbine and/or Sodium bicarbonate is added to the bioreactor prior to the production of biogas and/or Nitrogen is purged in the bioreactor for a time $t_5$ prior to the production of biogas, wherein the time $t_5$ is in a range of 20-40 min.

12. The method according to claim 3
characterized in that
the sewage sludge is in anaerobic condition at temperature $t_6$, wherein the temperature $t_6$ is room temperature.

13. The method according to claim 1
wherein the time $t_1$ is in a range of 24-48 h and/or the temperature $T_1$ is between 45° C.-55° C.

14. The method according to claim 5
characterized in that
the time $t_2$ is 5-15 min.

15. The method according to claim 1
characterized in that
the magnetic flux density is 0.2 mT and/or the time $t_3$ is in a range 3-5 h.

16. The method according to claim 9
characterized in that
the time $t_4$ is in a range of 19-23 days and/or the temperature $T_2$ is between 30° C.-39° C.

17. The method according to claim 11
characterized in that
the time $t_5$ is in a range of 25-35 min.

* * * * *